(12) United States Patent
Stewart

(10) Patent No.: US 6,475,504 B1
(45) Date of Patent: Nov. 5, 2002

(54) PEST REPELLENT COMPOSITIONS AND ARTICLES AND A METHOD FOR PREPARING THE SAME

(76) Inventor: Howard Franklin Stewart, 4700 Moorland Dr., Midland, MI (US) 48640

(*) Notice: Subject to any disclaimer, the term of this patent is extended or adjusted under 35 U.S.C. 154(b) by 0 days.

(21) Appl. No.: 08/547,748

(22) Filed: Oct. 25, 1995

(51) Int. Cl.[7] ............................................. A01N 25/32
(52) U.S. Cl. ..................... 424/406; 424/405; 424/409; 424/543; 424/548; 424/581; 424/DIG. 10; 424/76.3; 424/78.09; 524/10; 524/702; 524/704; 524/803; 523/122; 514/918; 514/919; 514/920
(58) Field of Search .................. 424/406, 408, 424/409, 438, 442, 543, 548, 581, DIG. 10, 76.3, 76.8, 78.09, 78.18, 78.31; 514/918–920; 521/141; 523/122; 524/10, 702, 704, 803

(56) References Cited

U.S. PATENT DOCUMENTS

| | | | |
|---|---|---|---|
| 4,110,431 A | * 8/1978 | Oita | 424/78 |
| 4,663,358 A | 5/1987 | Hyon et al. | |
| 4,818,535 A | * 4/1989 | Baines et al. | 424/407 |
| 4,888,364 A | 12/1989 | Graiver et al. | |
| 4,891,388 A | 1/1990 | Graiver et al. | |
| 4,891,389 A | 1/1990 | Graiver et al. | |
| 4,965,070 A | * 10/1990 | Messina | 424/581 |
| 4,996,067 A | * 2/1991 | Kobayami et al. | 426/96 |
| 5,063,232 A | * 11/1991 | Leyondedrer et al. | 514/247 |
| 5,437,870 A | * 8/1995 | Puritch et al. | 424/408 |
| RE35,660 E | * 11/1997 | Dyer, Sr. | 424/410 |

FOREIGN PATENT DOCUMENTS

| | | | |
|---|---|---|---|
| AU | 162953 | * | 5/1953 |
| JP | 7-230659 | * | 3/1988 |

OTHER PUBLICATIONS

Bar–Zeev: Materials Attractive or Repellent to Larvae of *Trogoderma granarium* Israel J. Entomol: 76(11)61–72
Feeds & Feeding: Morrison p 1954 pp. 595–597, 601.*

* cited by examiner

Primary Examiner—Neil S. Levy
(74) Attorney, Agent, or Firm—Robert L. McKellar

(57) ABSTRACT

What is disclosed is a method for the formation of unique poly(vinyl alcohol) hydrogels, articles that are made from such hydrogels, unique odor-providing pest repellent compositions and their uses to repel pests.

10 Claims, No Drawings

PEST REPELLENT COMPOSITIONS AND ARTICLES AND A METHOD FOR PREPARING THE SAME

This invention deals with pest repellent compositions and articles and a method for preparing both the compositions and the articles.

More specifically, this invention deals with poly(vinyl alcohol) hydrogels containing freezing point depressants, pest repellents, water and plasticizers which are capable of being formed into various configurations and shapes.

BACKGROUND OF THE INVENTION

Means and methods for repelling pests using certain forms of dispensers for the controlled release of repelling materials using volatile liquids such as perfumes, deodorants and biologically active compositions are well known.

Thus, such well known means and methods include an article comprising a reservoir of volatile liquid material enclosed within either a rigid or flexible container wherein at least a portion of the wall of the container is porous to the volatile liquid; the use of a dispenser which comprises a matrix, such as a film formed from a natural or synthetic organic polymer that is impregnated with the material to be released; the use of gels or waxes formed from a natural or synthetic organic polymer, and the like.

Such gel dispensers can be found in, for example, U.S. Pat. No. 4,888,364, issued Dec. 19, 1989 to Graiver, et al in which there is disclosed a free standing dispenser for the controlled release of volatile liquid materials such as perfumes and fragrances. The poly(vinyl alcohol) hydrogels used therein are described as those comprising a continuous phase of a solubilized poly(vinyl alcohol), a dispersed phase comprising a polyelectrolyte and an aqueous solution of the volatile liquid that is distributed between said continuous and dispersed phases. It is claimed that these dispensers remain dry to the touch throughout the useful life of the dispenser.

In another gel dispenser, disclosed in U.S. Pat. No. 4,891,388, which issued Jan. 2, 1990, to Graiver, et al, there is shown a method of preparing the gel dispenser, which method comprises forming a first solution by heating a mixture comprising poly(vinyl alcohol) and water and/or dimethyl sulfoxide under atmospheric pressure, adding a second solution comprising a volatile liquid material and a monohydric alcohol in a solvent that is miscible with the first solution under conditions that avoid precipitation of poly (vinyl alcohol), and then, cooling the resultant solution to below room temperature to form the gel. It appears that this disclosure provides the procedure for the preparation of the gel dispenser of the '364 patent.

Further, there is an identical disclosure in U.S. Pat. No. 4,891,389, which issued on Jan. 2, 1990 to Gravier. This patent is a divisional of the '364 patent and the disclosure is identical with the '364 patent.

The novelty in the aforementioned patents is the use of a polyelectrolyte with a certain poly(vinyl alcohol) hydrogel to provide compositions which are free standing. The poly (vinyl alcohol) materials used in those compositions and articles is that found in U.S. Pat. No. 4,663,358, which issued May 5, 1987 to Hyon, et al.

The U.S. Pat. No. 4,663,358 discloses the preparation of the hydrogels that have been found useful herein and that patent is incorporated herein by reference for what it teaches about the preparation of high strength poly(vinyl alcohol) hydrogels.

It should be understood by those skilled in the art that the inventor herein is relying on the general disclosure of the Hyon, et al patent and that a new and novel method for preparing the hydrogels of the instant invention is set forth and claimed herein.

THE INVENTION

The invention disclosed and described herein is a method for the formation of unique poly(vinyl alcohol) hydrogel compositions and unique odor-providing solid pest repellent compositions and their uses.

More specifically, one aspect of this invention deals with a process for preparing a solid pest repellent article capable of emitting a pest repelling odor. The process comprises (I) contacting a freezing point depressant for water with water and homogenizing the resulting solution at a temperature of 20° F. to 50° F. Thereafter, step (II) comprises heating the solution from (I) to a temperature of about 80° to about 100° C. and then (III) adding a high strength poly(vinyl alcohol) polymer and homogenizing once again. Step (IV) then comprises heating the solution of (III) until the solution is clear and essentially free of gel particles. It is at this point that one or more pest repellents can be added to the composition of (IV), and then in a step (V), the composition is further homogenized. Finally, in step (VI), the composition from (V) is frozen at a temperature of 0° C. or below for at least two hours to form a high strength poly(vinyl alcohol) hydrogel article. The freezing time can be less than two hours, but the articles will not be as strong or as tough. The frozen composition is then allowed to return to room temperature to provide the articles of this invention.

In another aspect of this invention, there is provided a composition comprising in combination a blend of a high strength poly(vinyl alcohol) hydrogel, water, at least one pest repellent, and, a water soluble, non-volatile, freezing point depressant for the water, which depressant does not de-stabilize the composition. The freezing point depressants are selected from a group consisting essentially of (a) inorganic salts, (b) organic solids, and (c) organic liquids.

And finally, a third aspect of this invention is an article or articles comprising solid pest repellents capable of emitting a pest repelling odor which comprises a combination of a high strength poly(vinyl alcohol) hydrogel, water, at least one pest repellent and a water soluble, non-volatile, freezing point depressant for the water wherein the freezing point depressant is selected from the group consisting essentially of (a) inorganic salts, (b) organic solids and, (c) organic liquids.

Turning first to the method by which the unique poly (vinyl alcohol) hydrogels are prepared, there is provided in step (I) a contact between one or more freezing point depressants for the water used in this method, and the water.

Such freezing point depressants are selected from water soluble, non-volatile, inorganic salts, water soluble, non-volatile, organic solids, and water soluble, non-volatile, organic liquids.

As can be observed, such depressants must be water soluble materials that can lower the freezing point of water and which will not de-stabilize the poly(vinyl alcohol) hydrogel when they are in contact. Using these freezing point lowering additives allows the preparation of the unique form of the poly(vinyl alcohol) hydrogel which is part of the invention herein.

Examples of inorganic salts that are useful in this invention include, generally, divalent metallic salts such as magnesium or calcium, for example calcium chloride ($CaCl_2$)

and magnesium chloride ($MgCl_2$). However, salts such a monovalent metallic salts of sodium, potassium, thallium, and lithium are not useful in the stabilizing of the poly(vinyl alcohol) hydrogels and are often used to break apart (solubilize) such materials, and are therefore, not part of this invention. An easy method to determine the usefulness of the inorganic salts is to test the ability of the salt to precipitate and/or solubilize the poly(vinyl alcohol) hydrogel. If the poly(vinyl alcohol) hydrogel precipitates or goes into solution, then the salt is not useful herein. Also, divalent transient metallic salts such as titanium, zirconium, copper, and cobalt can create complexes with the poly(vinyl alcohol) polymers resulting in water-insoluble, non-reversible gel formation and therefore, these materials are not useful in this invention. Further, trivalent metallic salts of boron, aluminum and the like are known to crosslink or complex with poly(vinyl alcohol) polymers also resulting in water insoluble gels, and therefore, these materials should also be avoided for use in this invention.

With regard to the organic water soluble materials, it should be noted that the materials, in order to be useful in this invention, must be water soluble, solids or liquids at room temperature, having the ability to lower the freezing point of water when put into solution and which do not de-stabilize the poly(vinyl alcohol) hydrogel.

For example, strongly ionic materials like amines, polyamines, phenolics, carboxylic acids and their salts are not suitable in this invention because they would de-stabilize the poly(vinyl alcohol) hydrogels. Other organics that would react with the poly(vinyl alcohol) hydrogels are aldehydes and paraformaldehyde. Non-ionic organic materials which are water soluble would be preferred.

Thus, materials that are useful in this invention as organic freezing point depressants are, for example, urea (which is also a plasticizer for the poly(vinyl alcohol) hydrogel and may play a dual role), sugars, water soluble starches, polyethylene oxides, acetone, alcohols, amides, glycerine, ethylene glycol, 1,3-dimethyl-2-imidazolidinone, dimethylsulfoxide, and the like.

The quantity of freezing point depressant that is useful in the compositions of the instant invention is such that the concentration of the additive be high enough to prevent water from freezing at the process temperatures used to gel the formulation. For example, calcium chloride should be used generally at about thirty percent solids of the compositions if the gelation temperature is −20° C. or less. The specific amount of the freezing point depressant depends on the selection of the additive and the desired physical properties of the final article.

These freezing point depressants are best used by first combining them with water and after the mixture is prepared, the composition is heated to a temperature of from about 80° C. to about 100° C., this temperature not being overly critical as the intent is to make a homogeneous composition. The amount of water useful in the compositions, and hence the articles, of this invention ranges from about 30 to about 80 weight percent based on the weight of the total composition.

Once the composition is homogeneous, then a high strength poly(vinyl alcohol) polymer is added to the composition and homogenized at the prevailing temperature in the range as set forth above, the intent of this step being to provide a homogeneous mixture. This composition is then heated until the composition is clear and essentially free of gel particles.

"Homogenizing" for purposes of this invention means converting the composition to a homogeneous composition which may be provided by simple stirring of the composition, or may be provided by other mechanical means.

"Non-volatile for purposes of this invention means organic materials with boiling points in excess of 100° C., or inorganic salts that do not vaporize, even at temperatures above 300° C.

At this point, one or more of the pest repellents is added and the composition is again homogenized. This composition is then frozen at a temperature of 0° C. or below for at least two hours to form small poly(vinyl alcohol) crystallites in the composition.

Finally, the composition, which is now a solid, having fully absorbed the water present in the composition, can be used to repel pests.

Pest repellents useful in this invention are those pest repellents that are available commercially and which are normally used for repelling pests. For example, insect repellents such as 2,ethyl-1,3-hexanediol or N,N-diethyl-meta-toluamide and the like are useful in this invention. These repellents are known to repel mosquitoes, black flies, chiggers and other biting flies and gnats.

Repellents for pest animals, for example, dogs, cats, other pets, and wildlife, such as skunks, deer, woodchuck and the like, must be chosen on the basis of performance of the repellent against the specific species. For example, white tailed deer are repelled from their typical foods by putting rotten eggs, feather meal, (which is a combination of feathers, bones, blood and eggs resulting from chicken and/or turkey processing), meat meal, and combinations of these materials in contact or close to their food source.

Typically, these repellents are used at 10 to 40 weight percent of the total solids of the repellent articles of this invention. The amount of repellent used in the article depends on the life expectancy, physical properties, application, and physical form of the article.

The articles of this invention can have any physical solid form depending on the end use of the article. For example, the article can be pellets, strips, molded articles, flat sheets, ribbons, and the like.

It should be noted that any extrusion, other forming, molding and the like must be performed on the composition as it exists at the end of step (V), and before the freezing step (VI). Once the composition from (V) is frozen, its ability to be extruded or otherwise formed is limited. Obviously, since the material can be cut, one method of providing articles of this invention which are long strips, is to pour the composition from step (V) onto a flat surface, such as a cookie sheet, and freezing, and then cutting the appropriate strips.

It should be noted that the compositions of this invention can be plasticized and if such is the case, then the plasticizer is added at the end of step (I), and before step (II).

Essentially any plasticizer known in the art of poly(vinyl alcohol) plastics technology is suitable in this invention. Examples of such materials are urea, glycerine, ethylene glycol, and the like. The choice of plasticizer and the amount used is dependent on the physical properties desired in the final article. If a softer, more pliant article is desired, then higher levels of plasticizer may be needed. Usage levels for the plasticizer in this invention range from zero to about seven percent by weight of the poly(vinyl alcohol) present in the composition.

The poly(vinyl alcohol) hydrogel of this invention is prepared from poly(vinyl alcohol) which is prepared by hydrolysis or saponification of polyvinyl acetate. The degree of hydrolysis of the alcohol varies depending upon the intended end use of the alcohol. The poly(vinyl alcohol) polymers useful in this invention are preferably those having a saponification of 95% or greater, it being preferred to use those having 99% or greater saponification and it is most preferred to use a material that is fully saponified.

The poly(vinyl alcohol) polymers useful in this invention are essentially linear or at the most contain a minimal degree of branching. It is believed by the inventor herein that this provides the highest degree of hydrogen bonding. The formation of hydrogen bonding between hydroxyl groups on adjacent polymer molecules and small crystal crystallization of the polymer are considered responsible for the development of the excellent physical properties associated with this type of gel. It is especially notable that these polymers have very small crystallite structures after they are frozen.

The molecular weight of the poly(vinyl alcohol) used to prepare the compositions and, ultimately, the articles of this invention is determined by the desired physical and aesthetic properties of the article. The molecular weight of the poly (vinyl alcohol) should not be less than about 60,000 grams/mole, preferably not less than about 80,000 and most preferred are those polymers of about 85,000 molecular weight and above.

Typically the properties of poly(vinyl alcohol) polymers, particularly tensile strength and elongation at break, increase with the increasing concentration and/or molecular weight of the polymer. Preferred in this invention are poly(vinyl alcohol) polymer concentrations of about 2% to 30% by weight based on the total solids concentration of the compositions.

EXAMPLE 1

Preparation of a Deer Repellent

The following procedure made a deer repellent for use in orchards and gardens.

The ingredients are as shown Table I.

TABLE I

| Ingredient | Weight (grams) | % |
|---|---|---|
| Airvol - 165* | 260 | 7.4 |
| Calcium chloride (77–80%)** | 600 | 17.1 |
| Urea, Fertilizer grade (plasticizer) | 70 | 2.0 |
| Water (tap water) | 1800 | 51.4 |
| Meat Meal (Tankage)*** | 750 | 21.4 |
| Pepper | 20 | 0.7 |

*Airvol$^R$ - 165 is poly (vinyl alcohol) from Air Products, Allentown, Pennsylvania
**Calcium Chloride is DowFlake$^R$ from Dow Chemical Co., Midland, Michigan.
***Tankage is from Morse Brothers Agriculture, Weidman, Michigan.

The preparation was carried out in a 20 quart porcelain open cooking vessel with constant stirring. The calcium chloride was slowly added to the water at room temperature over about a 15 minute period while being constantly stirred. The urea was then added quickly and the solution was heated to boiling. While boiling, the poly(vinyl alcohol) polymer was slowly added with stirring. This step required about 30 to 40 minutes. After the addition of the poly(vinyl alcohol) polymer was complete, the mixture was heated and stirred until the solution was clear and essentially free of gel particles. The solution at this stage was thick, and had a viscosity approximating the viscosity of honey. The meat meal and pepper were added to the solution and the mixture thickened and the heat was reduced. After the mixture was mixed and appeared homogeneous, it was poured into aluminum cookie sheets while still warm to form thin flat sheets. The cookie sheets were placed into a freezer at −20° C. until frozen, about 8 to 10 hours. The cookie sheets were then taken out of the freezer and the contents allowed to come to room temperature.

EXAMPLE 2

The flat sheets prepared in example 1 were cut into long narrow strips of about 3/16 to 1/4 inch wide and about 10 inches long. These strips were hand tied to the lower branches of apple trees, at the rate of 3 or 4 per tree, in an orchard located in the northeastern part of the State of Michigan known as the Brodhagen Orchards.

This, and an adjacent orchard on the Brodhagen farm were surveyed essentially on a daily basis for the presence of deer, and on a less frequent basis for signs of browsing by the deer on the apple trees.

Over a several month period, it was observed that not only was there a complete absence of browsing on the apple trees in the orchard provided with the articles of this invention, but it was also noticed that the deer would not even enter this orchard, while an adjacent apple tree orchard was observed to contain as many as 20 to 30 deer per day, and the browsing was extensive.

The advantages of the articles over current technology is that they exhibit a long life expectancy, have ease of use, are safe, in that, all of the materials of the compositions are environmentally green, the repellent does not contact the produce, there is no spraying required and the articles are low cost as compared to sprays and other application methods that are typically used in the industry.

I claim:

1. A composition consisting essentially of a blend of:
   (i) a high strength poly(vinyl alcohol) hydrogel;
   (ii) water;
   (iii) at least one solid pest repellent, and,
   (iv) a water soluble, non-volatile, freezing point depressant for (ii) which does not solubilize (i), complex (i), or de-stabilize the composition; said freezing point depressant being selected from a group consisting of:
      (a) inorganic salts and
      (b) organic solids.

2. A solid pest repellent capable of emitting a pest repelling odor consisting essentially of a blend of
   (i) a high strength poly(vinyl alcohol) hydrogel:
   (ii) water;
   (iii) at least one solid pest repellent, and,
   (iv) a water soluble, non-volatile, freezing point depressant for (ii) which does not solubilize (i). complex (i) or de-stabilize the blend, said freezing point depressant being selected from a group consisting of:
      (a) inorganic salts and
      (b) organic solids.

3. A solid pest repellent capable of emitting a pest repelling odor consisting essentially of a blend of
   (i) a high strength poly(vinyl alcohol) hydrogel;
   (ii) water;
   (iii) at least one solid pest repellent, and,
   (iv) a water soluble, non-volatile, inorganic salt, freezing point depressant for (ii) which does not solubilize (i), complex (i) or de-stabilize the blend.

4. A solid pest repellent capable of emitting a pest repelling odor consisting essentially of a blend of (i) a high strength poly(vinyl alcohol) hydrogel;

(ii) water;

(iii) at least one solid pest repellent, and, (iv) a water soluble, non-volatile, organic solid freezing point depressant for (ii) which does not solubilize (i), complex (i) or de-stabilize the blend.

5. A solid pest repellent article having the composition as claimed in claim 2.

6. A pest repellent as claimed in claim 2, wherein the pest repellent is a repellent for pest animals.

7. A pest repellent as claimed in claim 6, wherein the pest repellent is putrefied eggs.

8. A pest repellent as claimed in claim 6, wherein the pest repellent is feather meal.

9. A pest repellent as claimed in claim 6, wherein the pest repellent is meat meal.

10. A pest repellent as claimed in claim 6, wherein the pest repellent is meat meal tankage.

* * * * *